Figure 1:
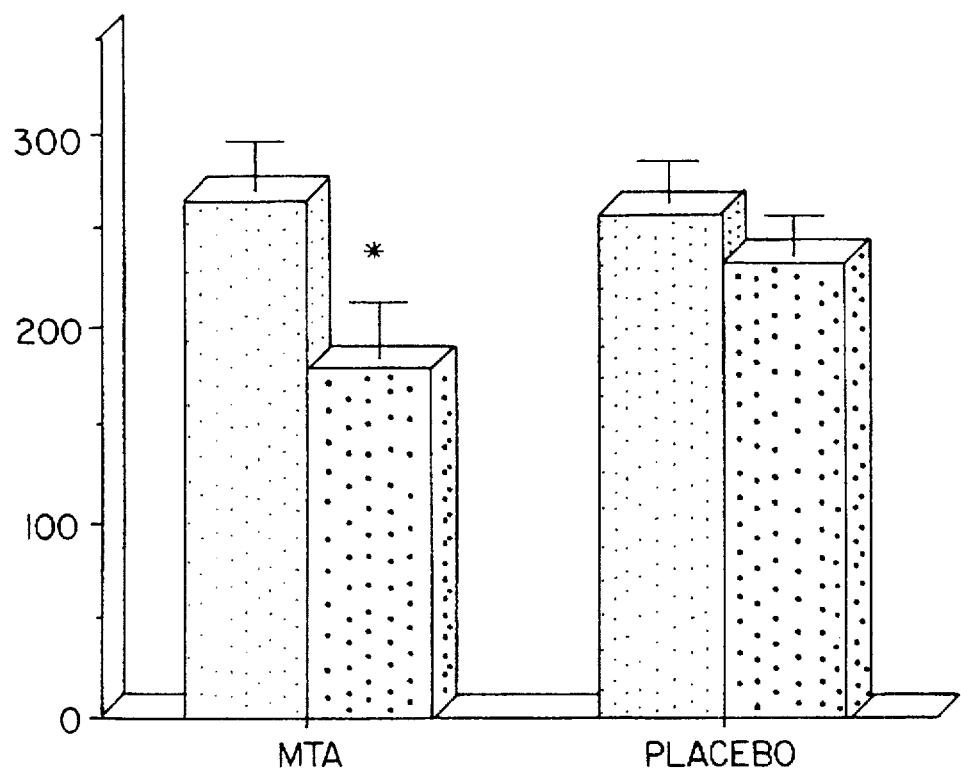

United States Patent [19]

Moratti

[11] Patent Number: 5,753,213
[45] Date of Patent: May 19, 1998

[54] PHARMACEUTICAL COMPOSITIONS CONTAINING 5'-DEOXY-5'-METHYLTHIOADENOSINE S-ADENOSYLMETHIONINE AND THEIR SALTS FOR REDUCING SEBORRHEA

[75] Inventor: Emanuela Maggioni Moratti, Bergamo, Italy

[73] Assignee: Bioresearch S.P.A., Milan, Italy

[21] Appl. No.: 492,991

[22] Filed: Mar. 13, 1990

[30] Foreign Application Priority Data

Mar. 13, 1989 [IT] Italy .................. 19737/89

[51] Int. Cl.$^6$ .................. A61K 7/06
[52] U.S. Cl. .................. 424/70.1; 514/45; 514/46; 514/852; 514/880; 514/881
[58] Field of Search .................. 514/44, 45, 49, 514/50, 46, 880, 881, 852; 424/70, 70.1

[56] References Cited

U.S. PATENT DOCUMENTS

| | | |
|---|---|---|
| 4,088,756 | 5/1978 | Voorhees . |
| 4,373,097 | 2/1983 | Stramentinoli et al. . |
| 4,496,588 | 1/1985 | Bey et al. .................. 514/564 |
| 4,670,255 | 6/1987 | Yoshizumi et al. . |
| 4,834,076 | 5/1989 | Millet et al. . |
| 4,956,173 | 9/1990 | LeFur et al. .................. 536/26 |

FOREIGN PATENT DOCUMENTS

| | | |
|---|---|---|
| 0072980 | 2/1983 | European Pat. Off. . |
| 0216357 | 4/1987 | European Pat. Off. . |
| 2277590 | 2/1976 | France . |
| 8705906 | 10/1987 | WIPO . |
| 8804301 | 6/1988 | WIPO . |

OTHER PUBLICATIONS

Hepatology, vol. 4, No. 2, 1984, pp. 274–278, Frezza et al.
Arch. Argent. Dermat., vol. 37, No. 1–16 2, 1987, pp. 75–81, Gomez et al.
Minerva Medica, vol. 66, No. 33, 1975, pp. 1600–1604, Gasbarrini et al.
Arch. Dermatol. Res, vol. 267, No. 2, 1980, pp. 196–197, Ruzicka et al.
Br. J. Pharmac. Res, vol. 60, 1977, pp. 583–587, Francis et al.
IL Gould Chiampo (1988) Zanichelli/McGraw-Hill, Bologna, p. 1130.
Mantero, M. et al. (Mantero), "Sindromi depressive, Mala Hil Cutanee e transmetilazioni," Gazzett Medical Italiana, vol. 135, No. 12 pp. 707–716 (1976).
Usman et al., J. of American Chem. Soc., vol. 109, see pages 7845–7854, (1987).
Rao et al., Tetrahedron Letters, vol. 28, No. 41, pp. 4897–4900, (1987).
Pon, Tetrahedron Letters, vol. 28, No. 32, pp. 3643–3646 (1987).
Morvan et al., Nucleic Acid Research, vol. 16, No. 3, pp. 833–847, (1988).

*Primary Examiner*—James O. Wilson
*Attorney, Agent, or Firm*—Birch, Stewart, Kolasch & Birch, LLP

[57] ABSTRACT

This invention relates to pharmaceutical compositions containing 5'-deoxy-5'-methylthioadenosine, S-adenosylmethionine and their pharmaceutically acceptable salts able to reduce scalp seborrhea and its related furfuraceous desquamation and pruritus.

12 Claims, 8 Drawing Sheets

PHARMACEUTICAL COMPOSITIONS CONTAINING 5'-DEOXY-5'-METHYLTHIOADENOSINE S-ADENOSYLMETHIONINE AND THEIR SALTS FOR REDUCING SEBORRHEA

This invention relates to pharmaceutical compositions containing 5'-deoxy-5'-methylthioadenosine (MTA), S-adenosylmethionine (SAMe) and their pharmaceutically acceptable salts able to reduce scalp seborrhea aid its related furfuraceous desquamation and pruritus.

Seborrhea (increased sebum production) is a very frequently encountered phenomenon which can manifest itself on the glabrous cutis (epidermis of greasy appearance) or on hair-containing zones. On the scalp in particular, the seborrhea is frequently accompanied by steatogenous furfuraceous desquamation often associated with pruritus and paresthesia of the capillitium. The hair becomes shiny, greasy and sticky.

Therapeutic uses of the product class comprising MTA and SAMe as antivirals, cytostatics and oncogenetic tissue transformation inhibitors are already known and widely described in the literature, such as in GB patent 1,555,991. Therapeutic uses of this product class as anti-inflammatories, antipyretics, platelet antiaggregants and sleep inducers are also known, as described in U.S. Pat. Nos. 4,454,122 and 4,373,097. Reference should be made to the aforesaid patents for descriptions of MTA and SAMe preparation processes.

Up to now no evidence exists confirming the ability of MTA or SAMe to reduce seborrhea. In fact, no pharmacological activity in the dermatological field has yet been demonstrated for MTA, while it has been casually observed with SAMe in a clinical investigation (Mantero M. & Pastorino P., 1976) performed on depressed patients.

In fact, two depressed patients in this investigation were also affected by psoriasis and showed a definite regression of the cutaneous syntomatology after parenteral SAMe treatment.

This therapeutic effect on the cutaneous affections characteristic of psoriasis was not ascribed, however, to a potential SAMe activity in the dermatological field but rather to its known antidepressant activity.

It is known in fact that psoriasis is in certain subjects attributable to a psychosomatic pathogenesis.

As to the itching symptom, some clinical trials effected with SAMe on women affected by intrahepatic cholestasis, during gestation (Frezza M. et al, 1984; Gomez M. L. et al, 1987), have shown the ability of said molecule to alleviate the symptom which seems to be strictly related to decrease of the biliary flux. The anti-itching effect of SAMe has therefore to be referred to its anti-cholestatic activity.

In conclusion, these three investigations cannot be related to the use of 5'-deoxy-5'-methylthioadenosine, S-adenosylmethionine and their salts in pharmaceutical preparations for seborrhea, which is characterized by a hyperproduction of sebum (Fitzpatrick T. B. & Bernhard J. D. The structure of skin lesions and fundamental of diagnosis, In: Dermatology in General Medicine, Edited by Fitzpatrick T. B., Eisen A. Z., Wolff K., Freedberg I. M., Austen K. F.; McGraw-Hill Book Company, 1987, p. 45), and cannot be necessarily correlated to an itching type, the origin of which does not depend on the conditions of the biliary flux and of the liver. MTA and SAMe scalp activity in reducing seborrhea and its related furfuraceous desquamation or pruritus has, however, never been described.

Many substances have been used up to the present time in the treatment of seborrhea and its frequently related manifestations (dandruff, pruritus), but most of these have proved to possess low therapeutic efficiency. The compositions which have proved of greatest efficiency are lotions containing low-power glucocorticosteroids, but these compositions are obviously difficult to manage because of the undesirable side effects which appear during protracted topical steroid therapy (such as acneform eruptions, cutaneous atrophy).

An object of the present invention is to describe and claim the use of MTA, SAMe and their salts in the preparation of pharmaceutical compositions which substantially reduce scalp seborrhea and its related furfuraceous desquamation and pruritus without inducing any negative side effect, and the pharmaceutical compositions concerned.

In this respect we have surprisingly found that pharmaceutical compositions containing as active principle MTA, SAMe or their salts according to the present invention are active in reducing scalp seborrhea and its related furfuraceous desquamation and pruritus.

This surprising pharmacological activity, in no way predictable on the basis of known pharmacological activities for these products, has been verified by numerous clinical trials. The results obtained in some of these clinical trials are reported hereinafter in order to illustrate the objects and advantages of the present invention.

Clinical Trial 1

50 subjects suffering from scalp seborrhea and furfuraceous desquamation took part in this clinical trial. The subjects, aged between 21 and 35 years, were divided into two balanced groups and were treated for one month with MTA administered orally at a dose of 600 mg/day or with placebo, in accordance with a double blind randomization scheme.

The effectiveness of the treatment in reducing seborrhea was evaluated in the following manner:

by a sebometer (mod. SM 810 Courage & Khazaka, Cologne, West Germany) to determine the sebum quantity present on the scalp.

by visual comparisons to quantify the following parameters: hair and scalp greasiness, dandruff, pruritus.

The sebometer is an apparatus which measures the sebum quantity present on the cutaneous surface based on the principle that an opaque window in the apparatus becomes more transparent the greater the quantity of greasy substance applied to it (method described by Schaefer and Kuhn Bussis in Arkiv für Klinische und Experimentelle Dermatologie 238, 429, 1970).

The apparatus sensor contains a strip (replacing the opaque window) of opaque plastics material of 0.1 mm thickness. Under that portion of the strip in use, of area 64 $mm^2$, there is a mirror which projects together with the strip by about 1 mm from the sensor. A spring is connected to the mirror to generate a constant pressure on that part of the cutis under examination. The strip surface, pressed in this manner against the cutaneous surface for 30 seconds, becomes more transparent by absorption of the sebum. The translucency of the window, which increases linearly with increase in the quantity of sebum absorbed, is measured by a photometer. The sebometric values can be converted into micrograms/$cm^2$ by a conversion table using the following equation:

$$\mu g/cm^2 = 0.66 \left[ 57 \left( 1 - e^{\frac{-(VS+13)}{160}} \right) \cdot \frac{3}{2} \right.$$

where VS=sebometric value, e=natural logarithm base= 2.718.

The effects of treatment with orally administered MTA on seborrhea, evaluated by the sebometer, are shown diagrammatically in FIG. 1. In FIG. 1 the vertical axis, on a scale from 0 to 300, represents the average sebometric values before treatment (histogram with light background) and after 1 month of treatment (histogram with dark background) in subjects treated with MTA or placebo. The asterisk indicates a significant difference of p<0.05 against the base value. The statistical analysis was effected by split-plot variance. A further comparison between groups and times was effected by the Tukey test.

From FIG. 1 it can be seen that there is a considerable and significant reduction in scalp seborrhea after oral treatment with MTA, whereas the placebo is ineffective.

Figure 2:
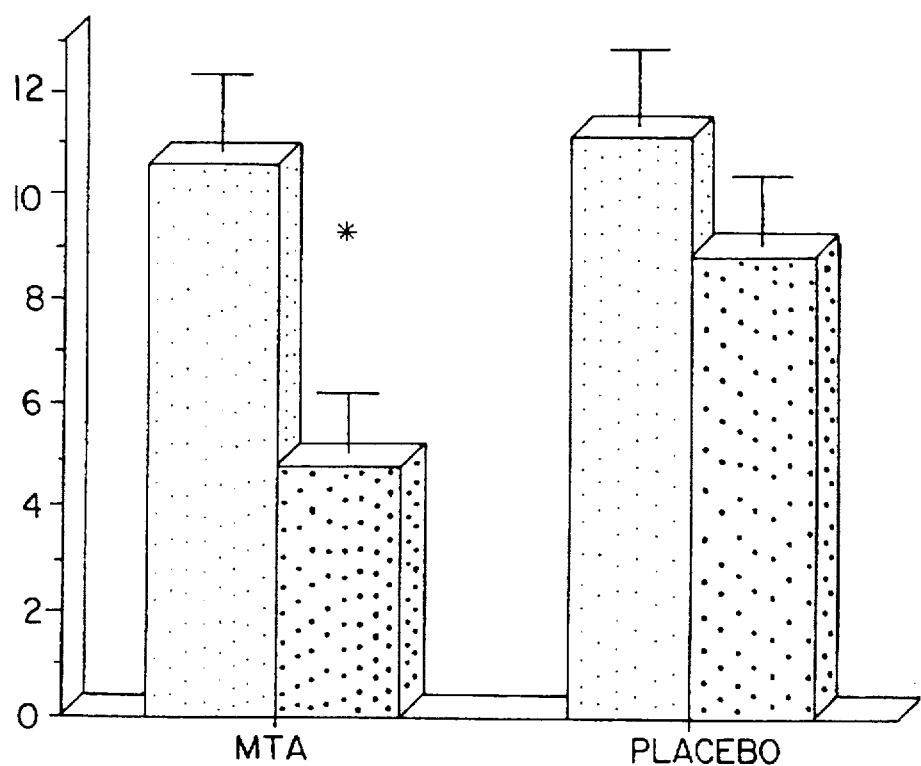
Figure 3:
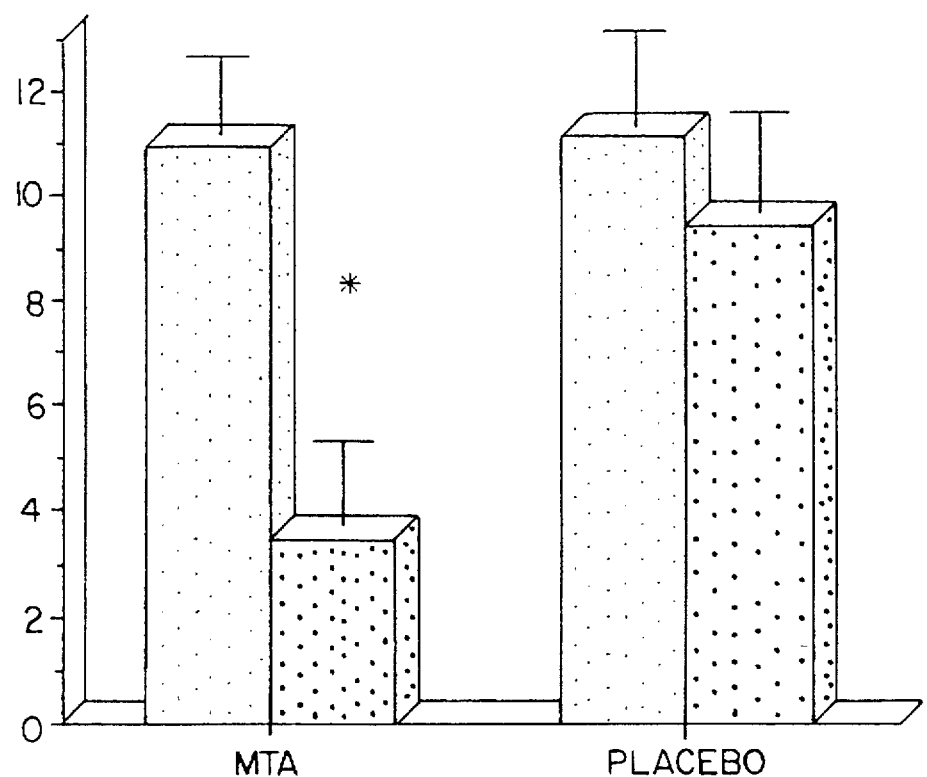
Figure 4:
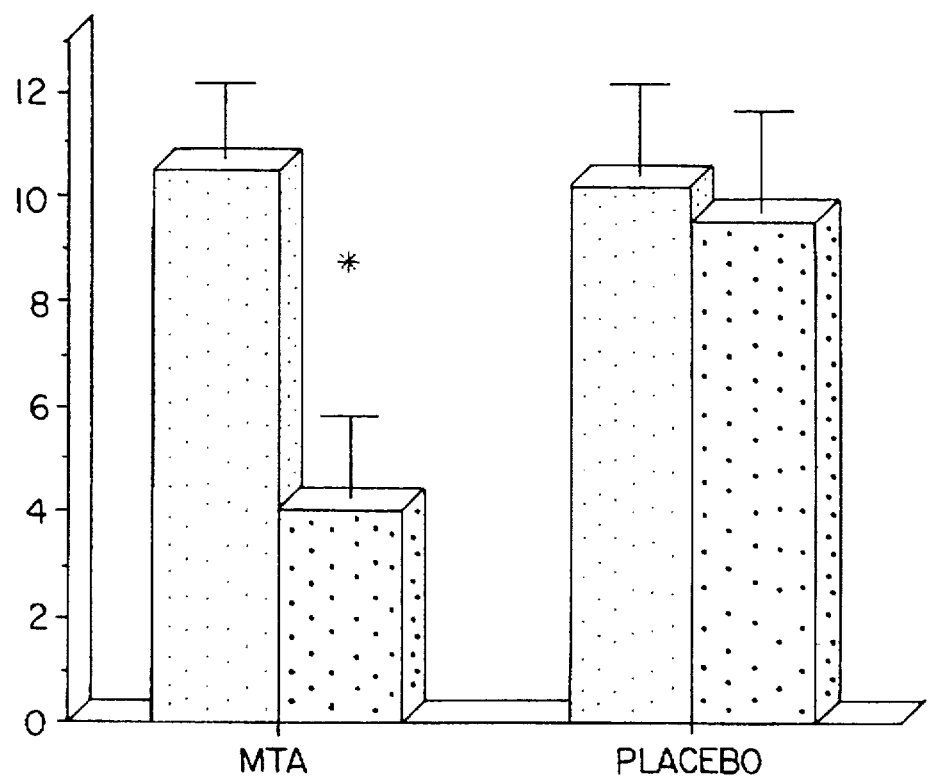

Hair and scalp greasiness, dandruff and pruritus were quantified on a comparison scale from 0 to 12 in which 0 represents absence of symptom and 12 its maximum expression. The average values before treatment (histogram with light background) and after treatment (histogram with dark background) for these 3 parameters for the groups of patients treated with MTA and placebo are shown in FIGS. 2, 3 and 4 respectively as mean±SD; the asterisk indicates a significant difference of p<0.05 against the base value. The statistical analysis was effected by split-plot variance. A further comparison between groups and times was effected by the Tukey test.

For each of these 3 parameters there is an obvious significant improvement after oral treatment with MTA.

Analogous trials were carried out using oral pharmaceutical compositions according to the present invention containing different doses of MTA and SAMe, namely 50 mg MTA (10 patients), 100 mg MTA (10 patients), 200 mg MTA (10 patients), 400 mg MTA (10 patients), 800 mg MTA (10 patients), 1200 mg MTA (10 patients), 1600 mg MTA (10 patients), 50 mg SAMe (10 patients), 100 mg SAMe (10 patients), 200 mg SAMe (10 patients), 400 mg SAMe (10 patients), 800 mg SAMe (10 patients), 1200 mg SAMe (10 patients) and 1600 mg SAMe (10 patients), it being found that pharmaceutical compositions containing these doses of active principle also produce significant improvements in the parameters considered.

Clinical Trial 2

50 subjects suffering from scalp seborrhea and dandruff and aged between 19 and 33 years took part in this clinical trial. The subjects were divided into two numerically equal groups and were treated for one month with a lotion for topical application containing MTA or with placebo, in accordance with a double blind randomization scheme.

The patients locally applied the lotion or placebo twice a day. During the clinical trial they were allowed to wash their hair once a week with a delicate shampoo which was identical in all cases.

The effectiveness of the treatment in reducing seborrhea was evaluated in the following manner:

by a sebometer (mod. SM 810 Courage & Khazaka, Cologne, West Germany) to determine the sebum quantity present on the scalp, by visual comparisons to quantify the following parameters: hair and scalp greasiness, dandruff, pruritus.

Figure 5:
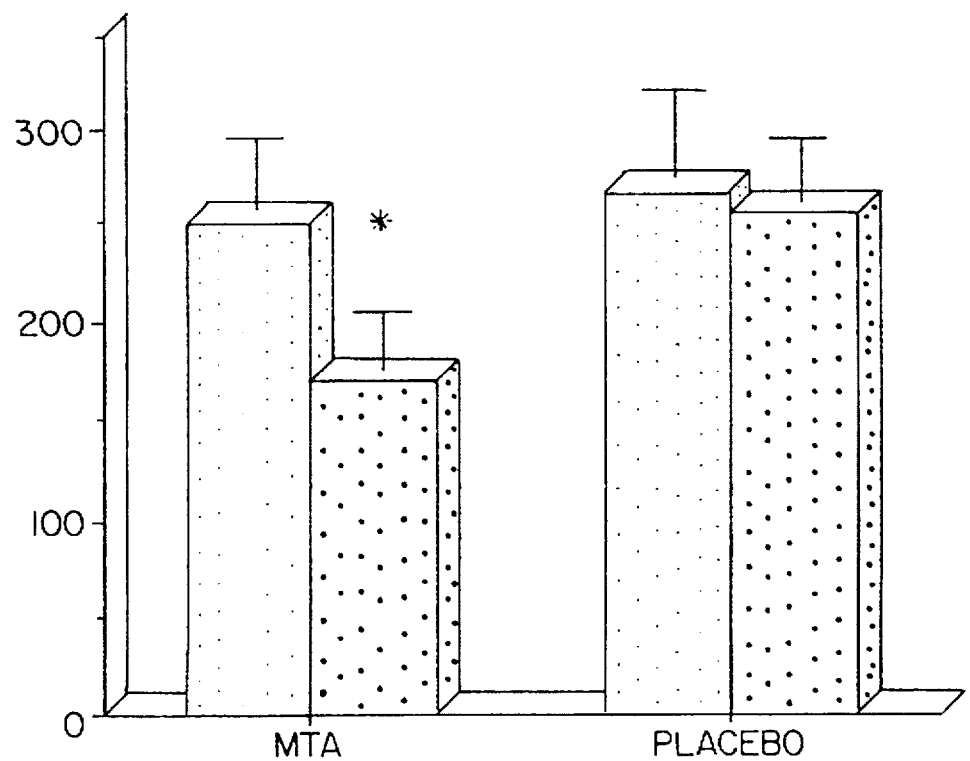

The effects of treatment with topically administered MTA on seborrhea, evaluated by the sebometer, are shown diagrammatically in FIG. 5. In FIG. 5 the vertical axis, on a scale from 0 to 300, represents the average sebometric values before treatment (histogram with light background) and after 1 month of treatment (histogram with dark background) in subjects treated with MTA or placebo. The asterisk indicates a significant difference of p<0.05 against the base value. The statistical analysis was effected by split-plot variance. A further comparison between groups and times was effected by the Tukey test.

From FIG. 5 it can be seen that there is a considerable and significant reduction in scalp seborrhea after topical treatment with MTA, whereas the placebo is ineffective.

Figure 6:
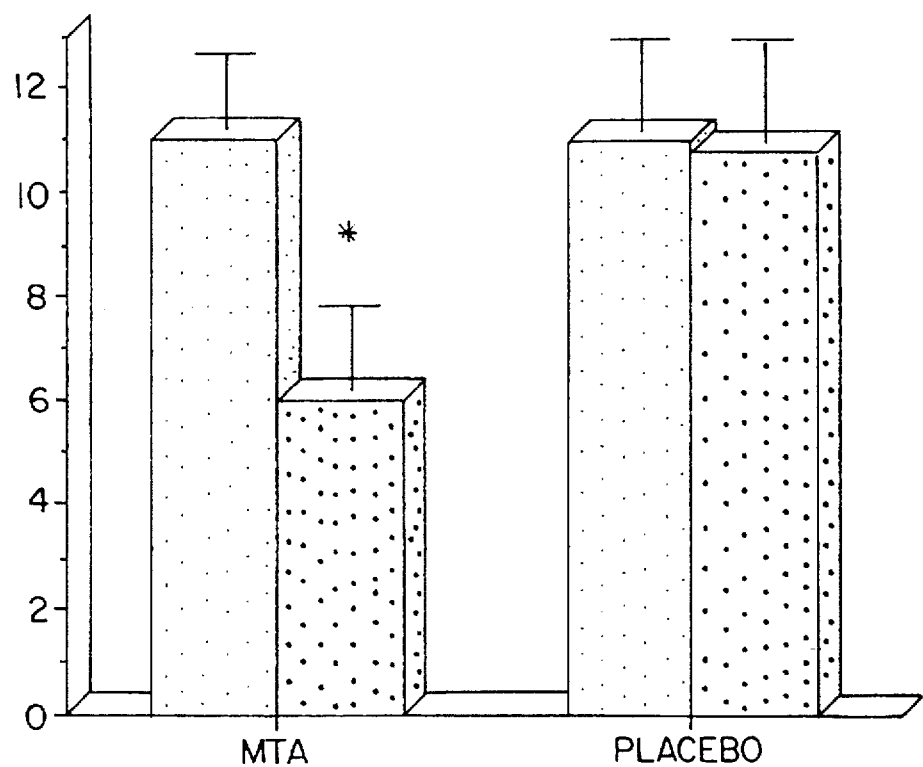
Figure 7:
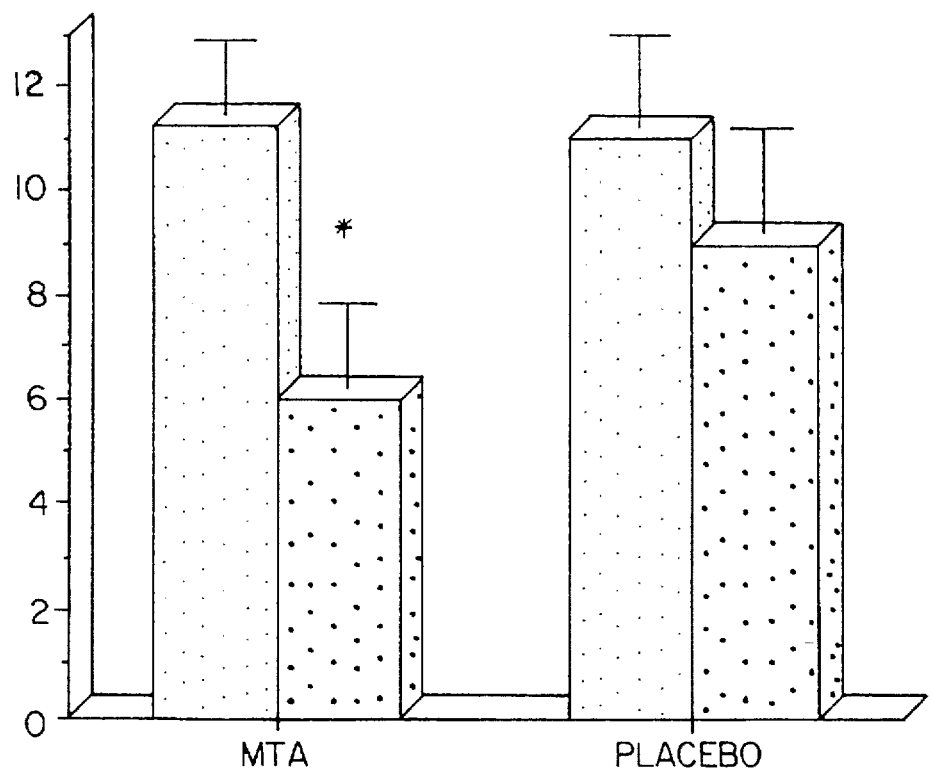
Figure 8:
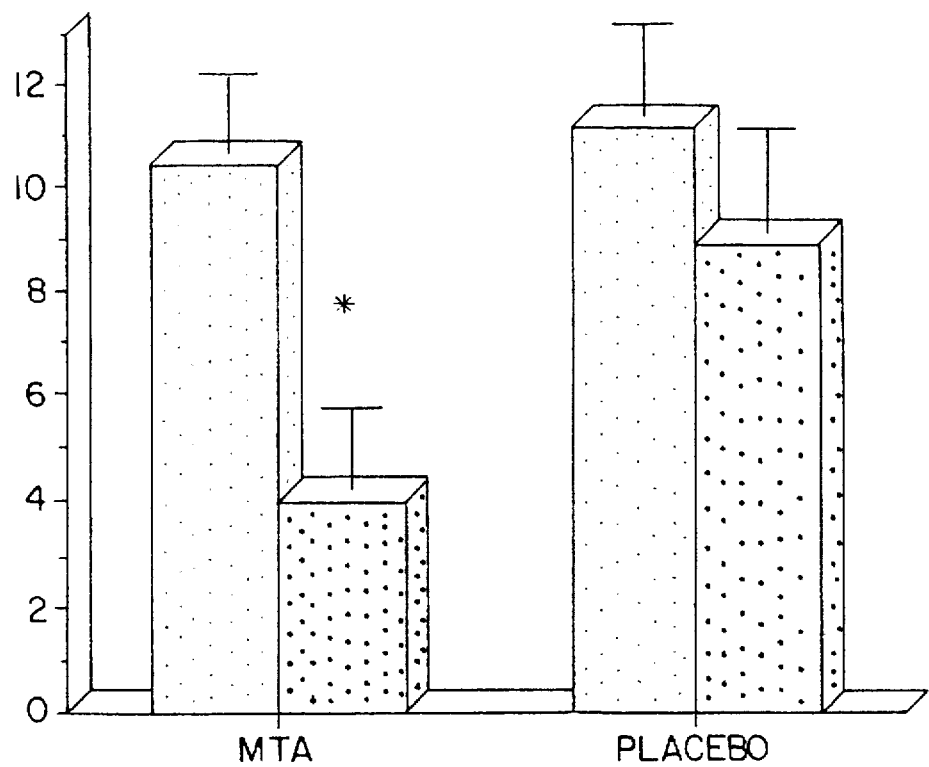

Hair and scalp greasiness, dandruff and pruritus were quantified on a comparison scale from 0 to 12 in which 0 represents absence of symptom and 12 its maximum expression. The average values before treatment (histogram with light background) and after treatment (histogram with dark background) for these 3 parameters for the groups of patients treated with MTA and placebo are shown in FIGS. 6, 7 and 8 respectively as mean±SD; the asterisk indicates a significant difference of p<0.05 against the base value. The statistical analysis was effected by split-plot variance. A further comparison between groups and times was effected by the Tukey test.

For each of these 3 parameters there is an obvious significant improvement after topical treatment with MTA.

Analogous trials were carried out using topical pharmaceutical compositions according to the present invention containing different doses of MTA and SAMe (the active principle content being expressed as % by weight of lotion), namely 0.1% MTA (10 patients), 1% MTA (10 patients), 2% MTA (10 patients), 3% MTA (10 patients), 4% MTA (10 patients), 5% MTA (10 patients), 0.4% SAMe (10 patients), 2% SAMe (10 patients), 4% SAMe (10 patients) and 8% SAMe (10 patients), it being found that pharmaceutical compositions containing these doses of active principle also produce significant improvements in the parameters considered.

In conclusion, the pharmaceutical compositions according to the present invention, suitable for both systemic and topical administration, have shown to be able to significantly reduce scalp seborrhea and its related furfuraceous desquamation, greasiness and pruritus, without inducing any negative side effect.

It should also be noted that the pharmaceutical compositions obtained using MTA or SAMe or their salts according to the present invention are practically free of acute toxicity when administered orally and are practically free of toxicity at the therapeutic doses for any manner of administration.

The compositions containing MTA according to the present invention and suitable for systemic administration can contain a quantity of active principle of between 50 and 1600 mg, and preferably between 600 and 1200 mg, whereas the compositions suitable for topical administration can contain a quantity of active principle of between 0.1 and 5% by weight, and preferably between 0.25 and 2% by weight, in association with the normally used pharmaceutical additives and excipients.

The compositions containing SAMe according to the present invention and suitable for systemic administration can contain a quantity of active principle of between 50 and 1600 mg, and preferably between 600 and 1200 mg, whereas the compositions suitable for topical administration can contain a quantity of active principle of between 0.2 and 16% by weight, and preferably between 2 and 8% by weight, in association with the normally used pharmaceutical additives and excipients.

Some examples of pharmaceutical compositions according to the present invention are given below for purposes of non-limiting illustration.

EXAMPLE 1

Tablet containing 50 mg of MTA 1 tablet contains:

| | |
|---|---|
| MTA sulphate (equivalent to 50 mg MTA) | 58.2 mg |
| Microcrystalline cellulose | 37.8 mg |
| Pregelatinized starch | 151.2 mg |
| Precipitated silica | 0.3 mg |
| Magnesium stearate | 2.5 mg |

EXAMPLE 2

Tablet containing 100 mg of MTA 1 tablet contains:

| | |
|---|---|
| MTA ascorbate (equivalent to 100 mg MTA) | 159.3 mg |
| Microcrystalline cellulose | 160.0 mg |
| Lactulose 100 mesh | 78.2 mg |
| Precipitated silica | 0.5 mg |
| Magnesium stearate | 2.0 mg |

EXAMPLE 3

Controlled-release tablet containing 200 mg of MTA

Release time=2 hours 1 tablet contains:

| | |
|---|---|
| MTA citrate (equivalent to 200 mg MTA) | 329.3 mg |
| Dibasic calcium phosphate dihydrate | 48.2 mg |
| Lactulose 100 mesh | 100.0 mg |
| Hydroxypropylmethylcellulose | 20.0 mg |
| Magnesium stearate | 2.5 mg |

EXAMPLE 4

Controlled-release tablet containing 400 mg of MTA

Release time=2 hours 1 tablet contains:

| | |
|---|---|
| MTA 1,4-butanedisulphonate (equivalent to 400 mg MTA) | 546.8 mg |
| Microcrystalline cellulose | 150.0 mg |
| Dibasic calcium phosphate dihydrate | 118.2 mg |
| Carboxyvinylpolymer | 25.0 mg |
| Glyceryl behenate | 10.0 mg |

EXAMPLE 5

Sachet containing 800 mg of MTA 1 sachet contains:

| | |
|---|---|
| MTA p-toluenesulphonate (equivalent to 800 mg MTA) | 1263.3 mg |
| Fructose | 1167.7 mg |
| Lactose 100 mesh | 500.0 mg |
| Precipitated silica | 6.0 mg |
| Aspartame | 10.0 mg |
| Flavour | 50.0 mg |
| Hydrogenated vegetable oil | 3.0 mg |

EXAMPLE 6

Gastroresistant tablet containing 200 mg of SAMe 1 tablet contains:

| | |
|---|---|
| SAMe sulphate p-toluenesulphonate (equivalent to 200 mg SAMe ion) | 384 mg |
| Mannite | 150 mg |
| Precipitated silica | 10 mg |
| Magnesium stearate | 6 mg |
| Cellulose acetophthalate | 15 mg |
| Diethylphthalate | 5 mg |

EXAMPLE 7

Gastroresistant tablet containing 400 mg of SAMe 1 tablet contains:

| | |
|---|---|
| SAMe 1,4-butanedisulphonate (equivalent to 400 mg SAMe ion) | 759.2 mg |
| Precipitated silica | 10.0 mg |
| Microcrystalline cellulose | 125.8 mg |
| Magnesium stearate | 5.0 mg |
| Cellulose acetophthalate | 26.2 mg |
| Diethylphthalate | 8.8 mg |

EXAMPLE 8

Injectable form containing 200 mg of SAMe 1 bottle contains:

| | |
|---|---|
| SAMe sulphate p-toluenesulphonate (equivalent to 200 mg SAMe ion) | 384 mg |
| Mannite | 200 mg |
| L-lysine | 300 mg |
| Sodium hydroxide | 9 mg |
| Water for injectable preparations | to make up to 5 ml |

EXAMPLE 9

Injectable form containing 400 mg of SAMe 1 bottle contains:

| | |
|---|---|
| SAMe 1,4-butanedisulphonate (equivalent to 400 mg SAMe ion) | 759.2 mg |
| L-lysine | 323.0 mg |
| Sodium hydroxide | 9.6 mg |
| Water for injectable preparations | to make up to 5 ml |

EXAMPLE 10

Controlled-release injectable form containing 400 mg of SAMe 1 bottle contains:

| | |
|---|---|
| SAMe 1,4-butanedisulphonate | 759.2 mg |
| (equivalent to 400 mg SAMe ion) | |
| Polyethyleneglycol 6000 | 100.0 mg |
| Hydroxyethylcellulose | 10.0 mg |
| L-lysine | 323.0 mg |
| Sodium hydroxide | 9.6 mg |
| Water for injectable preparations | to make up to 5 ml |

EXAMPLE 11

Controlled-release injectable form containing 200 mg MTA 1 bottle contains:

| | |
|---|---|
| MTA | 200 mg |
| Polysorbate 80 | 10 mg |
| Polyethyleneglycol 6000 | 100 mg |
| Water for injectable preparations | to make up to 5 ml |

EXAMPLE 12

Controlled-release suppository containing 400 mg MTA 1 suppository contains:

| | |
|---|---|
| MTA | 400 mg |
| Hydroxypropylmethylcellulose | 70 mg |
| Semisynthetic glycerides | 2530 mg |

EXAMPLE 13

Transdermic system containing 600 mg of MTA 1 system contains:

| | |
|---|---|
| MTA 1-4-butanedisulphonate | 820.2 mg |
| (equivalent to 600 mg MTA) | |
| Glycerin | 1400.0 mg |
| Polyvinyl alcohol | 350.0 mg |
| Polyvinylpyrrolidone | 175.0 mg |
| Purified water | 1575.0 mg |

EXAMPLE 14

Transdermic system containing 600 mg of SAMe 1 system contains:

| | |
|---|---|
| SAMe 1,4-butanedisulphonate | 1138.8 mg |
| (equivalent to 600 mg SAMe ion) | |
| Fluid silicone | 865.7 mg |
| Precipitated silica | 75.2 mg |

EXAMPLE 15

Lotion containing 0.25% of MTA 100 ml contain:

| | |
|---|---|
| MTA sulphate | 0.29 g |
| (equivalent to 0.25 g MTA) | |
| Methyl p-hydroxybenzoate | 0.15 g |
| Propyl p-hydroxybenzoate | 0.05 g |
| Purified water to make up to | 100 ml |

EXAMPLE 16

Lotion containing 0.5% of MTA 100 ml contain:

| | |
|---|---|
| MTA 1,4-butanedisulphonate | 0.68 g |
| (equivalent to 0.5 g MTA) | |
| Methyl p-hydroxybenzoate | 0.15 g |
| Propyl p-hydroxybenzoate | 0.05 g |
| Purified water to make up to | 100 ml |

EXAMPLE 17

Lotion containing 1% of MTA 100 ml contain:

| | |
|---|---|
| MTA citrate | 1.65 g |
| (equivalent to 1 g MTA) | |
| Methyl p-hydroxybenzoate | 0.15 g |
| Propyl p-hydroxybenzoate | 0.05 g |
| Purified water to make up to | 100 ml |

EXAMPLE 18

Spray lotion containing 0.5% of MTA 100 ml contain:

| | |
|---|---|
| MTA 1,4-butanedisulphonate | 0.68 g |
| (equivalent to 0.5 g MTA) | |
| Glycerin | 1.00 g |
| Ethyl alcohol | 5.00 g |
| Methyl p-hydroxybenzoate | 0.15 g |
| Propyl p-hydroxybenzoate | 0.05 g |
| Purified water to make up to | 100 ml |

EXAMPLE 19

Lotion containing 8% of SAMe 1 bottle contains:

| | |
|---|---|
| SAMe sulphate p-toluenesulphonate | 384.0 mg |
| (equivalent to 200 mg SAMe ion) | |
| Methyl p-hydroxybenzoate | 1.6 mg |
| Purified water | 2.5 ml |

EXAMPLE 20

Lotion containing 8% of SAMe
1 bottle contains:

| | |
|---|---|
| SAMe 1,4-butanedisulphonate (equivalent to 200 mg SAMe ion) | 379.6 mg |
| Methyl p-hydroxybenzoate | 1.6 mg |
| Purified water | 2.5 ml |

I claim:

1. A therapeutic method for treating a patient having scalp seborrhea and its related furfuraceous desquamation, associated with pruritus and paresthesia of the capillitium, comprising administering to said patient a scalp seborrhea reducing effective amount of a compound selected from the group consisting of 5'-deoxy-5'-methylthioadenosine, a pharmaceutically acceptable salt thereof, S-adenosylmethionine, and a pharmaceutically acceptable salt thereof.

2. The therapeutic method as claimed in claim 1, comprising administering topically a therapeutically effective amount of a compound selected from the group consisting of 5'-deoxy-5'-methylthioadenosine, a pharmaceutically acceptable salt thereof, S-adenosylmethionine, and a pharmaceutically acceptable salt thereof.

3. The therapeutic method as claimed in claim 1, wherein the content of said compound is between 50 and 1660 mg.

4. The therapeutic method as claimed in claim 1, wherein the content of said compound is between 600 and 1200 mg.

5. The therapeutic method as claimed in claim 1, wherein said compound is administered in the form of an aqueous solution, said administering is conducted topically, and wherein the content of said compound is between 0.1% and 5% by weight of said solution in the case of 5'-deoxy-5'-methylthioadenosine, and between 0.2% and 16% in the case of S-adenosylmethionine.

6. The therapeutic method as claimed in claim 1, wherein said compound is administered in the form of an aqueous solution, said administering parenterally is conducted topically, and wherein the content of said compound is between 0.25% and 2% by weight of said solution in the case of 5'-deoxy-5'-methylthioadenosine, and between 2% and 8% in the case of S-adenosylmethionine.

7. A therapeutic method for treating a patient having scalp seborrhea and its related furfuraceous desquamation, associated with pruritus and paresthesia of the capillitium, comprising administering to said patient a scalp seborrhea reducing effective amount of a compound selected from the group consisting of 5'-deoxy-5'-methylthioadenosine and a pharmaceutically acceptable salt thereof.

8. The therapeutic method as claimed in claim 7, comprising administering said compound topically.

9. The therapeutic method as claimed in claim 7, wherein the amount of said compound is between 50 and 1660 mg.

10. The therapeutic method as claimed in claim 7, wherein the amount of said compound is between 600 and 1200 mg.

11. The therapeutic method as claimed in claim 7, wherein said compound is administered in the form of an aqueous solution, and wherein the content of said compound is between 0.1% and 5% by weight of said solution.

12. The therapeutic method as claimed in claim 7, wherein said compound is administered in the form of an aqueous solution, and wherein the content of said compound is between 0.25% and 2% by weight of said solution.

* * * * *